(12) United States Patent
Koyama et al.

(10) Patent No.: US 7,767,236 B2
(45) Date of Patent: Aug. 3, 2010

(54) PLANT SEED EXTRACT COMPOSITION AND PROCESS FOR PRODUCING THE SAME

(75) Inventors: Naoto Koyama, Kawasaki (JP); Tetsuya Seki, Kawasaki (JP); Harumi Arisaka, Kawasaki (JP); Koichi Ishii, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 666 days.

(21) Appl. No.: 11/400,188

(22) Filed: Apr. 10, 2006

(65) Prior Publication Data

US 2006/0257540 A1    Nov. 16, 2006

Related U.S. Application Data

(63) Continuation of application No. PCT/JP2004/015087, filed on Oct. 6, 2004.

(30) Foreign Application Priority Data

Oct. 10, 2003    (JP)    ................... 2003-352829

(51) Int. Cl.
   *A61K 36/286*    (2006.01)
(52) U.S. Cl. .................... 424/776; 514/415
(58) Field of Classification Search .............. None
   See application file for complete search history.

(56) References Cited

U.S. PATENT DOCUMENTS

| 4,072,669 | A | * | 2/1978 | Betschart | ............... | 530/377 |
| 5,653,997 | A | * | 8/1997 | Renimel et al. | ............ | 424/450 |
| 7,357,951 | B2 | * | 4/2008 | Koyama et al. | ............ | 424/776 |
| 7,396,554 | B2 | * | 7/2008 | Jayalekshmy et al. | ....... | 426/629 |

FOREIGN PATENT DOCUMENTS

| JP | 54-130503 | | 10/1979 |
| JP | 10-287695 | | 10/1998 |
| KR | 2001034952 | * | 5/2001 |
| WO | WO 03/086437 A1 | | 10/2003 |

OTHER PUBLICATIONS

S.-H. Cho, et al., "Effects of Defatted Safflower Seed Extracts on Plasma and Liver Lipid in Ovariectomized Female Rats Fed High Cholesterol Diets", Faseb J., vol. 15, No. 5, 2002, A1011-737.21.

H.L. Zhang, et al., "Yuryo Shushi Ni Gan'Yu Sareru Kosanka Busshitsu No Kenkyu -Benibana Aburakasu Oyobi Menjitsu Aburakasu Ni Gan'Yu Sareru Kosanka Busshitsu No Tansaku", Symposium on the chemistry of Natural Products, Symposium papers, vol. 39, 1997, pp. 559-564 w/English Abstract.

H.L. Zhang, et al., "Antioxidative Compounds Isolated From Safflower (*Carthamus tinctorius* L.) Oil Cake", Chem. Pharm. Bull., vol. 45, No. 12, 1997, pp. 1910-1914.

S. Kawashima, et al., "Serotonin Derivative, N-(P-Coumaroyl) Serotonin, Inhibits the Production of TNF-A, IL-1A, IL-1B, and IL-6 by Endotoxin-Stimulated Human Blood Monocytes", Journal of Interferon and Cytokine Research, vol. 18, 1998, pp. 423-428.

J.H. Kim, et al., "Lignan From Safflower Seeds Induces Apoptosis in Human Promyelocyctic Leukemia Cells", Nutraceuticals & Food, vol. 8, 2003, pp. 113-118.

R. Palter, et al., "A Cathartic Lignan Glycoside Isolated From *Carthamus tinctorus*", Phytochemistry, vol. 11, No. 9, 1972, pp. 2871-2874.

R. Tasneem, et al., "Effect of Aqueous Ethanol Washing on the Physicochemical and Functional Properties of Safflower (*Carthamus tinctorius*) Seed Proteins", J. Sci. Food Agric., vol. 59, 1992, pp. 237-244.

B. Fuhrman, et al., "Consumption of Red Wine With Meals Reduces the Susceptibility of Human Plasma and Low-Density Lipoprotein to Lipid Peroxidation", Am. J. Clin. Nutr., vol. 61, 1995, pp. 549-554.

S. Renaud, et al., "Wine, Alcohol, Platelets, and the French Paradox for Coronary Heart Disease", The Lancet, vol. 339, Jun. 20, 1992, pp. 1523-1526.

J. Yamakoshi, et al., "Proanthocyanidin-Rich Extract From Grape Seeds Attenuates the Development of Aortic Atherosclerosis in Cholesterol-Fed Rabbits", Atherosclerosis, vol. 142, 1999, pp. 139-149.

J. Fruebis, et al., "Extent of Antioxidant Protection of Plasma LDL Is Not a Predictor of the Antiatherogenic Effect of Antioxidants", Journal of Lipid Research, vol. 38, 1997, pp. 2455-2464.

J. Fruebis, et al., "Effect of Vitamin E on Atherogenesis in LDL Receptor-Deficient Rabbits", Atherosclerosis, vol. 117, 1995, pp. 217-224.

(Continued)

*Primary Examiner*—Susan C Hoffman
(74) *Attorney, Agent, or Firm*—Oblon, Spivak, McClelland, Maier & Neustadt, L.L.P.

(57) ABSTRACT

Plant seed extract compositions obtained by washing a defatted plant seed with water, and extracting the resulting washed seed product with an organic solvent and safflower seed extract compositions wherein the weight ratio of the total content of (a) p-coumaroylserotonin, feruloylserotonin, p-coumaroylserotonin glycoside, and feruloylserotonin glycoside to (b) 2-hydroxyarctiin is 1:0.01 to 0.2, are effective for reducing the risk of developing atherosclerosis and diseases caused by atherosclerosis and also exhibit a reduced tendency to cause diarrhea.

25 Claims, 3 Drawing Sheets

OTHER PUBLICATIONS

J.S. Munday, et al., "Dietary Antioxidants Do Not Reduce Fatty Streak Formation in the C57BL/L Mouse Atherosclerosis Model", Arterioscler. Thromb. Vasc. Biol., vol. 18, 1998, pp. 114-119.

K.-D. Moon, et al., "Safflower Seed Extract Lowers Plasma and Hepatic Lipids in Rats Fed High-Cholesterol Diet", Nutrition Research, vol. 21, 2001, pp. 895-904.

C.K. Lyon, et al., "Removal of Deleterious Glucosides From Safflower Meal", Journal of the American Oil Chemists' Society, vol. 56, 1979, pp. 560-564.

Lin Rui-Yu, et al. "A Study on Preparation of Saponins and Active Carbon from Oil-tea-cakes" Quarterly of Forest By-Product and Speciality in China, Nov. 2001, No. 4, pp. 5-6.

Yoshihiro Hotta et al.; "Protective effects of antioxidative serotonin derivatives isolated from safflower against postischemic myocardial dysfunction"; Molecular and Cellular Biochemistry, vol. 238, 2002; pp. 151-162.

Sung-Hee Cho et al; "Effects of Defatted Safflower Seed Extract and Phenolic Compounds in Diet on Plasma and Liver Lipid in Ovariectomized Rats Fed High-Cholesterol Diets"; Journal of Nutritional Science and Vitaminology, vol. 50, 2004; pp. 32-37.

Jung-Seop Roh et al. "In Vitro Antioxidant Activity of Safflower (*Carthamus tinctorius* L.) Seeds"; Food Sci. Biotechnol., vol. 8, No. 2, 1999; pp. 88-92.

\* cited by examiner (*rapeseed meal and safflower meal were 200-fold diluted while others were 50-fold diluted)

(a-1)

(b-1)

(c-1)

PLANT SEED EXTRACT COMPOSITION AND PROCESS FOR PRODUCING THE SAME

CROSS REFERENCES TO RELATED APPLICATIONS

This application is a continuation of International Patent Application No. PCT/JP2004/015087, filed on Oct. 6, 2004, and claims priority to Japanese Patent Application No. 2003-352829, filed on Oct. 10, 2003, both of which are incorporated herein by reference in their entireties.

BACKGROUND OF THE INVENTION

1. Field of the Invention

The present invention relates to novel plant seed extract compositions that can be used for the prophylaxis, etc., of atherosclerosis. The present invention also relates to foods, feeds, and pharmaceutical compositions, which contain such a plant seed extract composition. The present invention further relates to methods of producing such a plant seed extract composition.

2. Discussion of the Background

Along with the westernization of life style in recent years, in addition to cancer, atherosclerotic diseases such as angina pectoris, cardiac infarction, cerebral infarction, and the like have become the main causes of death of Japanese people. A consensus has been generally reached that oxidation of LDL (low density lipoprotein) plays a key role in the early stages of lesion formation, and the importance of not only controlling the blood cholesterol level to a suitable range but also suppressing the production of oxidized LDL has been pointed out recently.

It has been clarified that foods, particularly a food derived from plants, contain an abundance of anti-oxidative substances, and the anti-oxidative substances contained in green tea and red wine are considered to be taken into LDL (or in the vicinity thereof) and eliminate radicals to prevent production of oxidized LDL (Fuhrman et al, *Am. J. Clin. Nutr.*, vol. 61, pp. 549-54 (1995)). There is also an epidemiological study that concludes that a positive intake of these foods suppresses cancer and heart diseases (Renaud et al, *Lancet* vol. 339, pp. 1523-26 (1992)).

In the meantime, there is a report that particular components derived from particular seeds such as sesame seed lignan, grapeseed polyphenol, and the like show an anti-atherosclerotic activity with experimental animals (Kang et al, *J. Nutr.*, vol. 129, pp. 1885-90 (1999) and Yamakoshi et al, *Atherosclerosis*, vol. 142, pp. 139-49 (1999)). However, the anti-atherosclerotic property of a plant seed component has been clarified at an animal test level only in a few cases, and many researches remain at a test tube level. For example, JP-A-8-337536 discloses an anti-active oxygen agent extracted from a roasted and then fermented plant seed. The technique uses a plant seed as a starting material, but has low versatility because it requires operations such as roasting, fermentation treatment and the like, and, thus, this technique is not practical. In addition, the effect of suppressing atherosclerosis is not clearly shown. Furthermore, Zhang et al (Zhang et al, *Chem. Pharm. Bull.*, vol. 45, pp. 1910-14 (1997)) report structures of a group of compounds extracted from a safflower oil cake by distribution of various solvents, and that some of these structures have an antioxidant activity in vitro. However, it is not clear at present if such compounds having an antioxidant activity are effective for preventing atherosclerosis. In consideration of the fact that antioxidant activity in vitro is known not to be necessarily correlated to the anti-atherosclerotic activity in vivo (Fruebis et al, *J. Lipid Res.*, vol. 38, pp. 2455-64 (1997); Fruebis et al, *Atherosclerosis, vol.* 117, pp. 217-24 (1995); and Munday et al, *Arterioscler. Thromb. Vasc. Biol.*, vol. 18, pp. 114-19 (1998)), confirmation of whether or not an anti-oxidative substance in a plant seed has anti-atherosclerotic property is required at least at an experimental animal level. Moon et al. found an action of suppressing an increase of blood cholesterol in rats fed with a cholesterol-loaded feed in a powder, ethanol extract, or hot water extract of safflower seed (Moon et al, *Nutr. Res.*, vol. 21, pp. 895-904 (2001)). However, the results of the cholesterol-loading test using the rats show evaluation of the suppression of cholesterol absorption, rather than the suppression of atherosclerosis.

On the other hand, safflower seed is known to contain a serotonin derivative known to show in vitro antioxidant activity and anti-inflammatory activity (Zhang et al., *Chem. Pharm. Bull.*, vol. 44, pp. 874-876 (1996) and Kawashima et al., *J. Interferon Cytokine Res.*, vol. 18, pp. 423-428 (1998)). Furthermore, some of the safflower seeds are known to contain a serotonin derivative (glycoside) (Zhang et al., *Chem. Pharm. Bull.*, vol. 45, pp. 1910-14 (1997)). Moreover, safflower seed has been reported to contain a serotonin derivative and, as a diarrhea-inducing substance, a phenolic glycoside (2-hydroxyarctiin) (Palter. R. et al., *Phytochemistry*, vol. 11, pp. 2871-2874 (1972)). While 2-hydroxyarctiin has been reported to be extractable with water at pH 5, the behavior of serotonin derivatives has not been examined (Lyon. C. K. et al., *J. Amer. Oil Chem. Soc.*, vol. 56, pp. 560-564 (1979)).

SUMMARY OF THE INVENTION

Accordingly, it is one object of the present invention to provide novel plant seed extract compositions.

It is another object of the present invention to provide novel plant seed extract compositions which contain a large amount of an ingredient which is active in vivo.

It is another object of the present invention to provide novel plant seed extract compositions which is associated with fewer side effects.

It is another object of the present invention to provide novel plant seed extract compositions which exhibits a reduced tendency to cause diarrhea.

It is another object of the present invention to provide novel foods, which contain such a plant seed extract composition.

It is another object of the present invention to provide novel feeds, which contain such a plant seed extract composition.

It is another object of the present invention to provide novel pharmaceutical compositions, which contain such a plant seed extract composition.

It is another object of the present invention to provide novel methods of producing such a plant seed extract composition.

It is another object of the present invention to provide novel methods of producing such a plant seed extract composition, which is suitable for the production of foods, feeds, and pharmaceutical compositions.

Of the present inventors, Koyama et al. have found that an organic solvent extract of a defatted plant seed, particularly, safflower seed and rapeseed, (extract obtained by washing an aqueous ethanol extract of a defatted seed with hexane and extracting same with ethyl acetate) suppresses in vitro oxidization of LDL in human plasma and, an organic solvent extract of a defatted plant seed suppresses formation of atheromatous plaque (plaque) on a blood vessel inner wall of mouse in vivo, and is effective for the prophylaxis of atherosclerosis in experimental animal (PCT/JP03/04607). In addition, of the present inventors, Koyama et al. have found that a mixture of serotonin derivatives (p-coumaroylserotonin and feruloylserotonin) is effective for the prophylaxis of atherosclerosis in experimental animals (PCT/JP03/04607). From this finding, it is easily assumed that, like these serotonin derivatives, a serotonin derivative, which is a glycoside known to be contained in a safflower seed, shows activity in vivo and is effective for the prophylaxis of atherosclerosis.

For prevention of atherosclerosis, diarrhea is harmful. In view of the above-mentioned situation and finding, the present inventors took note of the development of a plant seed extract composition, which has a high content of a serotonin derivative having activity in vivo and effective for the prophylaxis of atherosclerosis, and a low content of 2-hydroxyarctiin, which is a diarrhea-inducing substance, as well as an extraction method for producing the composition.

The present inventors have conducted intensive studies in an attempt to solve the aforementioned problems and found that a composition having a high content of a serotonin derivative and a low content of 2-hydroxyarctiin can be obtained by washing a defatted plant seed with water and extracting, with an organic solvent, the obtained product after the washing treatment, which resulted in the completion of the present invention. Since the method of the present invention can be performed using agents for production, which are generally usable for the production of foods, feeds and pharmaceutical compositions, it is suitable for the production of foods, feeds and pharmaceutical compositions.

Thus, the present invention provides:

(1) A plant seed extract composition obtained by washing a defatted plant seed with water, and extracting the resulting seed with an organic solvent.

(2) A plant seed extract composition obtained by washing a defatted plant seed with water, extracting the resulting seed with an organic solvent, and concentrating and drying the extract.

(3) The composition of the above-mentioned (1) or (2), wherein the plant seed is a seed of safflower.

(4) A safflower seed extract composition wherein the weight ratio of the total content of p-coumaroylserotonin, feruloylserotonin, p-coumaroylserotonin glycoside and feruloylserotonin glycoside:2-hydroxyarctiin is 1:0.01 to 0.2.

(5) The composition of the above-mentioned (4), which is obtained by washing a defatted safflower seed with water, and extracting the resulting seed with an organic solvent.

(6) The composition of the above-mentioned (4), which is obtained by washing a defatted safflower seed with water, extracting the resulting seed with an organic solvent, and concentrating and drying the extract.

(7) The composition of the above-mentioned (1), (2), (3), (5) or (6), wherein the organic solvent is a lower alcohol.

(8) The composition of the above-mentioned (7), wherein the lower alcohol is ethanol.

(9) A food comprising the composition of any one of the above-mentioned (1) to (8).

(10) A feed comprising the composition of any one of the above-mentioned (1) to (8).

(11) A pharmaceutical composition comprising the composition of any one of the above-mentioned (1) to (8).

(12) A method of producing a plant seed extract composition, which comprises washing a defatted plant seed with water, and extracting the resulting seed with an organic solvent.

(13) A method of producing a plant seed extract composition, which comprises washing a defatted plant seed with water, extracting the resulting seed with an organic solvent, and concentrating and drying the extract.

(14) The method of the above-mentioned (12) or (13), wherein the plant seed is a seed of safflower.

(15) The method of the above-mentioned (12), (13) or (14), wherein the organic solvent is a lower alcohol.

(16) The method of the above-mentioned (15), wherein the lower alcohol is ethanol.

The plant seed extract composition of the present invention is a novel composition having a high content of a serotonin derivative, which is an active ingredient, and a low content of 2-hydroxyarctiin, which is a diarrhea-inducing compound. According to the method of the present invention, the above-mentioned plant seed extract composition can be preferably produced, and since the method of the present invention does not require ethyl acetate, which is generally unpreferable for use as an agent for the production of foods, feeds, and the like, it is suitable for the production of food, feed and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2 is a sketch for the purpose of clarifying the red stained part thereof by drawing a figure of the photograph and blacked out the red stained part.

DETAILED DESCRIPTION OF THE PREFERRED EMBODIMENTS

Figure 1:
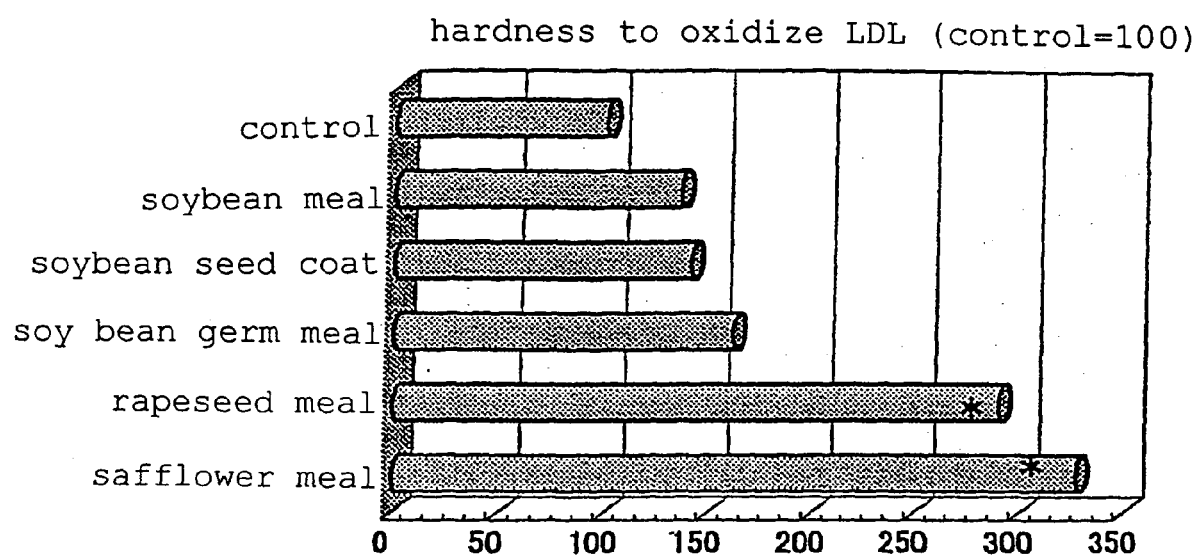
FIG. 1 is a graph showing an effect on the oxidizability of LDL in each sample of Reference Example 1.

The plant seed to be used in the present invention may be a seed of any plant, and, for example, seeds of safflower, rapeseed, soybean, and the like can be mentioned, with preference given to the seeds of safflower. In the present invention, a plant seed means the whole constituting a plant seed, or a part thereof, such as seed coat, albumen, germ, and the like, or a mixture thereof.

In the present invention, plant seed after defatting, or a defatted material (meal), is used as a starting material. A defatted material of plant seed can be obtained by delipidating the plant seed by a method known per se. For example, the material can be obtained by press-extracting seeds or adding n-hexane and the like to a crushed seed, extracting the mixture, taking out a solid content from the extraction system and drying the solid content. The degree of defatting is generally not less than 60% by weight, preferably not less than 80% by weight.

The present invention is characterized in that a defatted plant seed, which is a starting material, is washed with water before the below-mentioned extraction with an organic solvent.

The water to be used is not particularly limited and, for example, distilled water, tap water, industrial water, and mixed water thereof, and the like can be used. As long as the effect of the present invention can be afforded, the water may contain other substances, such as inorganic salts (e.g., sodium chloride, potassium chloride, calcium chloride, etc.), acids (e.g., hydrogen chloride, acetic acid, carbonic acid, hydrogen peroxide, phosphoric acid, etc.), alkali (e.g., sodium hydroxide, potassium hydroxide, sodium hydrogen carbonate, etc.) and the like. For washing, the pH of the water is generally 2 to 9, preferably 5 to 7.

The total amount of water to be used is generally a 2- to 100-fold amount (water volume (e.g., liters)/defatted plant seed weight/mass (e.g., kg), hereinafter the same), preferably 10- to 40-fold amount, relative to the defatted plant seed (starting material).

Washing can be conducted by contacting a defatted plant seed (starting material) with water according to a method known per se. For example, a method comprising suspending a defatted plant seed in water, and recovering a solid after washing treatment by filtration can be mentioned. For washing, the above-mentioned amount of water may be brought into contact with the defatted plant seed at once or multiple times, or continuously. The contact temperature for the washing is generally 5 to 45° C., preferably 25 to 35° C. The contact time is generally 10 to 240 minutes, preferably 15 to 60 minutes.

The present invention is characterized in that the defatted plant seed after washing treatment as obtained above is extracted with an organic solvent to give a plant seed extract composition.

The organic solvent is exemplified by, but not limited to, lower alcohols, acetone, mixed solvents thereof, and the like. The organic solvent may contain water or may be anhydrous. The concentration of the organic solvent is generally 20 to 95 wt %, preferably 50 to 90 wt %. From the aspects of concentration of the extract after extraction, drying and food production, the organic solvent is preferably a lower alcohol. The lower alcohol is exemplified by, but not limited to, alcohols having 1 to 4 carbon atoms, such as methanol, ethanol, n-propanol, isopropanol, n-butanol, and the like. From the aspect of food production, the lower alcohol is preferably ethanol. As ethanol, aqueous ethanol containing ethanol in an amount of not less than 50 wt % or anhydrous ethanol is preferable.

The amount of the organic solvent to be used is generally 2- to 40-fold amount (organic solvent volume (e.g., liters)/defatted plant seed weight/mass (e.g., kg), hereinafter the same), preferably 2- to 10-fold amount, relative to the defatted plant seed (starting material). The extraction temperature is generally 20 to 75° C., preferably 50 to 70° C. The extraction time is generally 10 to 240 minutes, preferably 60 to 120 minutes.

After extraction, the solid content is separated from the suspension by filtration and the like, and the obtained extract can be used as it is or, where necessary, concentrated, dried and used as the plant seed extract composition of the present invention. For concentration and drying, the extract may be concentrated and dried as it is, or an excipient (e.g., lactose, sucrose, starch, cyclodextrin, etc.) may be added. While the composition extracted with the above-mentioned solvent is useful as the plant seed extract composition of the present invention at the purity it has, it may be further purified by a method known per se.

When the plant seed extract composition of the present invention obtained by the above-mentioned method is used as a food, a feed, or a pharmaceutical composition (atherosclerosis preventive agent, etc.) and when the composition is present in a physiologically harmful solvent, the composition may be dried, or the dry product may be dissolved, suspended, or emulsified in a physiologically acceptable solvent. The form of a composition includes a liquid such as an aqueous solution and the like, a solid obtained by concentration under reduced pressure and drying, a solidified product such as a lyophilized product, and the like.

The plant seed extract composition of the present invention obtained by the above-mentioned method characteristically has a high total content of serotonin derivatives (e.g., p-coumaroylserotonin, feruloylserotonin, p-coumaroylserotonin glycoside, and feruloylserotonin glycoside, etc.), and a low content of 2-hydroxyarctiin. As used herein, when an excipient is added, the content means an amount excluding the added excipient. Of the plant seed extract compositions of the present invention obtained by the above-mentioned method, for example, a safflower seed extract composition contains generally 10 to 70 wt %, preferably 20 to 50 wt %, total of p-coumaroylserotonin, feruloylserotonin, p-coumaroylserotonin glycoside, and feruloylserotonin glycoside, relative to the total amount of the plant seed extract composition, and generally not more than 20 wt %, preferably not more than 5 wt %, of 2-hydroxyarctiin, relative to the total amount of the plant seed extract composition, though subject to change depending on the purity and the like of the composition. Moreover, of the plant seed extract compositions of the present invention obtained by the above-mentioned method, for example, a safflower seed extract composition has a weight ratio of (a) the total amount of p-coumaroylserotonin, feruloylserotonin, p-coumaroylserotonin glycoside, and feruloylserotonin glycoside to (b) 2-hydroxyarctiin of generally 1:0.05 to 0.2, preferably 1:0.01 to 0.2.

The present invention also relates to a novel safflower seed extract composition having a weight ratio of (a) the total amount of p-coumaroylserotonin, feruloylserotonin, p-coumaroylserotonin glycoside, and feruloylserotonin glycoside to (b) 2-hydroxyarctiin of 1:0.05 to 0.2, preferably 1:0.01 to 0.2. The novel safflower seed extract composition of the present invention can be preferably produced by the above-mentioned method of the present invention.

In the present invention, the serotonin derivative content refers to a value obtained by monitoring UV 290 nm by high performance liquid chromatography with Capcell Pak C18 column manufactured by Shiseido and using linear gradient of aqueous acetonitrile as a developing solvent, and determining the amount by comparison with a standard sample. In the present invention, the 2-hydroxyarctiin content refers to a value obtained by monitoring UV 279 nm by high performance liquid chromatography with Capcell Pak C18 column manufactured by Shiseido and using linear gradient of aqueous acetonitrile as a developing solvent, and determining the amount by comparison with a standard sample.

The plant seed extract composition of the present invention, particularly a safflower seed extract composition, has a high content of a serotonin derivative, and therefore, can be used for the treatment or prophylaxis of diseases for which administration or intake, or prophylactic administration or intake, of a serotonin derivative is effective, for example, for the prophylaxis of atherosclerosis and the like. In addition, the plant seed extract composition of the present invention, particularly a safflower seed extract composition, has a low content of 2-hydroxyarctiin, which is a diarrhea-inducing substance, and therefore, is associated with a fewer side effects. Consequently, the plant seed extract composition of the present invention, particularly a safflower seed extract composition, is extremely useful as a pharmaceutical composition such as a prophylactic agent for atherosclerosis and the like, a food for the prophylaxis of atherosclerosis and the like, and a feed for the prophylaxis of atherosclerosis and the like.

The plant seed extract composition, particularly safflower seed extract composition of the present invention prevents atherosclerosis and is useful for preventing diseases caused by atherosclerosis, such as angina pectoris, cardiac infarction, intermittent claudication, cerebral infarction, and the like. In other words, administration of the present plant seed extract composition or a food, feed, or pharmaceutical composition containing the present plant seed extract composition is effective for reducing the risk of developing atherosclerosis and diseases caused by atherosclerosis, such as angina pectoris, cardiac infarction, intermittent claudication, cerebral infarction, and the like.

The plant seed extract composition of the present invention is advantageously applied to human, animals other than human (e.g., mammals other than human (domestic animals including porcine, bovine, horse, canine, feline, and the like), birds (poultries including turkey, chicken, and the like) etc.), and the like.

The "food" of the present invention means food in general, and includes a general food including health food, Food for Specified Health Use, and Food with Nutrient Function Claims as defined in the Food with Health Claims System of the Health, Labor and Welfare Ministry, and encompasses supplements.

As the food, feed, or pharmaceutical composition, the plant seed extract composition itself of the present invention can be used. In addition, it is possible to use the plant seed extract composition of the present invention contained in various foods, for example, general food (including what is called health food) such as dressing, mayonnaise, and the like. Moreover, the composition of the present invention can be prepared into tablets, pills, granules, fine granules, powders, pellets, capsules, solutions, emulsions, suspensions, syrups, troches, and the like together with excipients (e.g., lactose, sucrose, starch, etc.), and, in some cases, with flavorings, dyes, and the like, and used as Food with Health Claims such as Food for Specified Health Use, Food with Nutrient Function Claims and the like, supplement, or pharmaceutical preparation (pharmaceutical composition)(mainly for oral use). In addition, the plant seed extract composition of the present invention can be also applied to the use for feed, and can be given or administered to poultries, domestic animals, and the like by adding to a regular feed.

Particularly, in the case of a pharmaceutical composition, the composition can be prepared along with a pharmaceutically acceptable carrier (including additive). Examples of the pharmaceutically acceptable carrier include, but are not limited to, excipients (e.g., lactose, sucrose, starch, D-mannitol, etc.), binders (e.g., cellulose, sucrose, dextrin, hydroxypropyl cellulose, polyvinylpyrrolidone, etc.), disintegrants (e.g., starch, carboxymethyl cellulose, etc.), lubricants (e.g., magnesium stearate, etc.), surfactants (e.g., sodium lauryl sulfate, etc.), solvents (e.g., water, brine, soybean oil, etc.), preservatives (e.g., p-hydroxybenzoate, etc.) and the like, which are known to those of ordinary skill in the art.

While the amount of intake or dose of the plant seed extract composition of the present invention varies depending on the purity of the composition, age, body weight, health condition, and kinds of diseases of the subject, and the like, for example, generally 10 mg to 10 g, preferably 100 mg to 10 g, is preferably given or administered to an adult per day for the prevention of atherosclerosis, which is given once a day or in several portions a day.

Since the plant seed extract composition produced by the method of the present invention uses plant seeds which are conventionally used for food and the like (particularly, seeds of safflower used as a starting material of cooking oil), and the content of a diarrhea-inducing substance is small, the toxicity is extremely low and the side effects are scarcely observed.

Other features of the invention will become apparent in the course of the following descriptions of exemplary embodiments which are given for illustration of the invention and are not intended to be limiting thereof.

EXAMPLES

Example 1

A defatted safflower seed (safflower meal) (0.1 kg) was measured in a container equipped with a stirrer, water (0.5 L) was added, and the mixture was stirred at 30° C. for 30 minutes. The contents were applied to a filtration centrifuge (200 g) at room temperature to separate the contents into a solid content and washing. The solid content was washed four times with water (0.5 L×4). To the meal (0.17 kg) after washing was added aqueous ethanol (water:ethanol=1:9, weight ratio) solution (0.5 L), and the mixture was stirred at 60° C. for 1 hour. The contents were applied to a filtration centrifuge (200 g) to separate the contents into a solid content and an extract (0.5 L). The extract (0.5 L) was concentrated under reduced pressure and dried in vacuo to give a safflower meal extract (2.7 g).

Example 2

A defatted safflower seed (safflower meal) (0.1 kg) was measured in a container equipped with a stirrer, water (0.5 L) was added, and the mixture was stirred at 30° C. for 30 minutes. The contents were applied to a filtration centrifuge (200 g) at room temperature to separate the contents into a solid content and washing. The solid content was washed four times with water (0.5 L×4). To the meal (0.17 kg) after washing was added aqueous ethanol (water:ethanol=5:5, weight ratio) solution (0.5 L), and the mixture was stirred at 60° C. for 1 hour. The contents were applied to a filtration centrifuge (200 g) to separate the contents into a solid content and an extract (0.5 L). The extract (0.5 L) was concentrated under reduced pressure and dried in vacuo to give a safflower meal extract (2.4 g).

Example 3

A defatted safflower seed (safflower meal) (0.1 kg) was measured in a container equipped with a stirrer, water (2 L) was added, and the mixture was stirred at 30° C. for 30 minutes. The contents were applied to a filtration centrifuge (200 g) at room temperature to separate the contents into a solid content and washing. To the meal (0.17 kg) after washing was added aqueous ethanol (water:ethanol=1:9, weight ratio) solution (0.5 L), and the mixture was stirred at 60° C. for 1 hour. The contents were applied to a filtration centrifuge (200 g) to separate the contents into a solid content and an extract (0.5 L). The extract (0.5 L) was concentrated under reduced pressure and dried in vacuo to give a safflower meal extract (2.4 g).

Comparative Example 1

To a defatted safflower seed (safflower meal) (0.1 kg) was added aqueous ethanol (water:ethanol=1:9, weight ratio) solution (0.5 L), and the mixture was stirred at 60° C. for 3 hours. The contents were applied to a filtration by suction to separate the contents into a solid content and an extract (0.5 L). As a second step, this extract (0.5 L) was concentrated under reduced pressure and dissolved in water (0.1 L). The aqueous solution (0.1 L) was washed with hexane (0.1 L), ethyl acetate (0.1 L) was added, and the mixture was mixed and partitioned to give an ethyl acetate layer. The ethyl acetate extract was concentrated under reduced pressure and dried in vacuo to give a safflower meal extract (1.2 g).

Example 4

Analysis and Evaluation of Safflower Meal Extract

The safflower meal extracts produced in the respective examples were analyzed by the following methods, and the amounts of p-coumaroylserotonin (CS), feruloylserotonin (FS), p-coumaroylserotonin glycoside (CS-Glc), feruloylserotonin glycoside (FS-Glc), and 2-hydroxyarctiin were analyzed. The results are shown in Tables 1 to 3.

TABLE 1

Analysis results of extract of Example 1

| per 1 g | mg |
|---|---|
| CS-glc | 110 |
| FS-glc | 45 |
| CS | 103 |
| FS | 102 |
| 2-hydroxyarctiin | 32 |

TABLE 2

Analysis results of extract of Example 2

| per 1 g | mg |
|---|---|
| CS-glc | 74 |
| FS-glc | 51 |
| CS | 50 |
| FS | 52 |
| 2-hydroxyarctiin | 42 |

TABLE 3

Analysis results of extract of Comparative Example 1

| per 1 g | mg |
|---|---|
| CS-glc | 67 |
| FS-glc | 15 |
| CS | 88 |
| FS | 71 |
| 2-hydroxyarctiin | 61 |

Analysis of the Serotonin Derivatives.

A safflower meal extract (5 mg) was dissolved and dispersed in ethanol (50 ml). This dispersion was used as an analysis sample. This analysis sample was subjected to high performance liquid chromatography under the following conditions, and the contents of the serotonin derivatives were analyzed. For the standard sample of p-coumaroylserotonin and feruloylserotonin, those obtained by condensation of serotonin and trans-4-coumaric acid or trans-4-ferulic acid were used. As standards for p-coumaroylserotonin glycoside and feruloylserotonin glycoside, those obtained by the method described in *Chemical and Pharmaceutical Bulletin.* vol. 45, pp. 1910-1914 (1997) were used.

Conditions of High Performance Liquid Chromatography:
   stationary phase: Shiseido Capcell Pak C18 5 µm
   column diameter: 4.6 mm, column length: 250 mm
   developing solvents: from 0.1% aqueous trifluoroacetic acid solution to 0.1% trifluoroacetic acid-40% aqueous acetonitrile solution, linear gradient for 40 minutes
   developing solvent flow rate: 1 ml/minute
   detector: UV (290 nm)

Analysis of 2-hydroxyarctiin.

The safflower meal extract (5 mg) of each example was dissolved and dispersed in ethanol (50 ml). This dispersion was used as an analysis sample. This analysis sample was subjected to high performance liquid chromatography under the following conditions, and the content of 2-hydroxyarctiin was analyzed. As the standard sample for 2-hydroxyarctiin, one obtained by the method described in *Journal of the American Oil Chemists' Society*, vol. 35, pp. 560-564 (1978) was used.

Conditions of High Performance Liquid Chromatography:
   stationary phase: Shiseido Capcell Pak C18 5 µm
   column diameter: 4.6 mm, column length: 250 mm
   developing solvents: from 0.1% aqueous trifluoroacetic acid solution to 0.1% trifluoroacetic acid-40% aqueous acetonitrile solution, linear gradient for 40 minutes
   developing solvent flow rate: 1 ml/minute
   detector: UV (279 nm)

Example 5

The safflower meal extracts (composition of Table 1 and composition of Table 3, suspended in 0.5% carboxymethylcellulose) were orally administered once to rats (SD(IGS), male, 7-week-old), and the presence or absence of diarrhea and soft feces was directly confirmed on a feces plate for 24 hours after administration. The results are shown in Table 4.

As is clear from Table 4, all the rats to which the sample of Comparative Example 1, which was free of water washing, (composition of Table 3), was orally administered showed diarrhea at 1,000 mg/kg, but the rats to which the sample of Example 1 (the present invention), which was extracted after water washing, (composition of Table 1), was orally administered showed no effect at 200 mg/kg and only 2/7 rats showed diarrhea even at a high dose of 1,000 mg/kg, thus showing improved cathartic effect.

TABLE 4

| safflower meal extract | dose (mg/kg) | |
|---|---|---|
| composition | 200 | 1000 |
| Comparative Example 1 (composition of Table 3) | N.T. | diarrhea = 3/3 |
| Example 1 (composition of Table 1) | diarrhea × soft feces = 0/7 | diarrhea = 2/7, soft feces = 2/7 |

N.T.: Not tested

Reference Example 1

In vitro Anti-oxidation Data

To defatted safflower meal (100 g) was added 500 ml of aqueous ethanol containing 90 vol % of ethanol, and the mixture was warmed and stirred in hot water bath at 60° C. for 3 hour, and filtered. The solid content after filtration was subjected to a similar step once, and the obtained filtrates were combined and concentrated under reduced pressure to give 60 ml of concentrated solution. Water was added to the concentrated solution to make 200 ml, and the contents were suspended, which was washed twice with 120 ml of n-hexane. The aqueous layer after washing was extracted twice with ethyl acetate (100 ml). The ethyl acetate extract solution was washed with saturated brine, the ethyl acetate layer was dried over anhydrous magnesium sulfate, and filtered and concentrated under reduced pressure to give a solid (1.16 g). Simultaneously, defatted rapeseed meal, soybean meal, soybean germ meal and soybean seed coat were respectively subjected to a similar treatment, 1 ml of DMSO was added to 1/10 amount of an extract for dissolution and used as samples.

Plasma obtained from human volunteer (adjusted to density=1.21 (g/ml) with KBr) was subjected to discontinuous density gradient centrifugation (417,000 H g, 40 minutes, 4° C.)(OptimaTLX; Beckman Coulter), and an LDL band was withdrawn with a syringe. The protein content of the LDL fraction was measured (BCA protein assay kit; Pierce biotechnology, Inc.), and diluted with phosphate buffer (PBS) to a final concentration of 100 μg protein/ml. Thereto was added a 1/100 amount of the above-mentioned sample, and a radical initiator (V70; 2,2'-azobis(4-methoxy-2,4-dimethylvaleronitrile)) was added to a final concentration of 1 mM. The absorption at 234 nm based on the conjugated diene structure in lipid peroxide was immediately monitored for 5 hours (DU640; Beckman Coulter). The lag time was calculated according to the method of Kondo et al. (*J. Nutr. Sci. Vitaminol.*, vol. 43, pp. 435-44 (1997)) based on the obtained lipid peroxide production curve. The effect of each sample on the oxidizability of LDL was evaluated by a relative value of the lag time with that of control (solvent alone was added) as 100 (see, FIG. 1). Every sample tended to more or less suppress oxidizability of LDL (i.e., extension of lagtime), but rapeseed meal and safflower meal particularly strongly suppressed the oxidation of LDL. The dilution fold of each sample before mixing with diluted human LDL in the above-mentioned test was 200-fold for rapeseed meal and safflower meal, and 50-fold for others.

Reference Example 2

In vivo Atherosclerosis Preventive Effect

Extracts of rapeseed meal and safflower meal were prepared as follows.

To defatted rapeseed meal (600 g) was added 3000 ml of aqueous ethanol containing 90 vol % of ethanol, and the mixture was warmed and stirred in hot water bath at 60° C. for 3 hours, and filtered. The solid content after filtration was subjected to a similar step once, and the obtained filtrates were combined and concentrated under reduced pressure to give 500 ml of concentrated solution. Water was added to the concentrated solution to make the amount 1000 ml and the contents were suspended, which was followed by washing twice with 500 ml of n-hexane. The aqueous layer after washing was extracted twice with ethyl acetate (500 ml). The ethyl acetate extract solution was dried over anhydrous magnesium sulfate, filtered, and concentrated under reduced pressure to give an extract (12.5 g).

The defatted safflower meal (600 g) was treated in the same manner as above to give 10.1 g of an extract.

Figure 2:
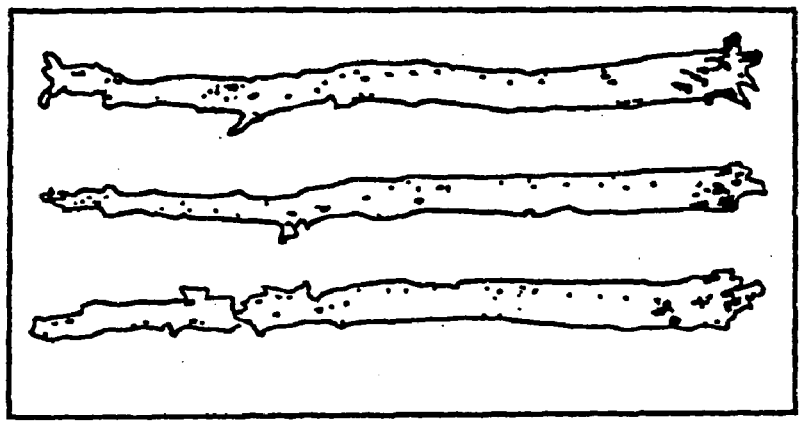
FIG. 2 is a sketch of a photograph showing that a safflower meal extract composition and a rapeseed meal extract composition have a suppressive effect on atherosclerosis in the aorta of apoE (−/−) mice (atherosclerosis model mice)(week 5 of administration, 14-week-old) in Reference Example 2, wherein (a-1) is a control group, (b-1) is a safflower group and (c-1) is a rapeseed group. The photograph is originally a color photograph and the part stained in red shows an atheromatous plaque.
Figure 2:
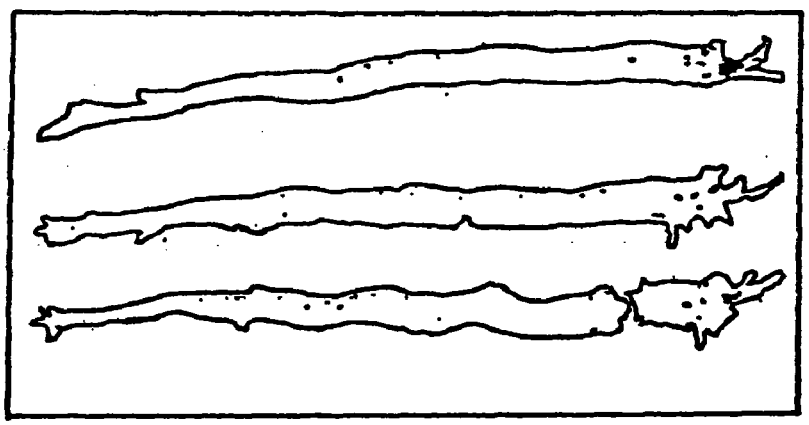
Figure 2:
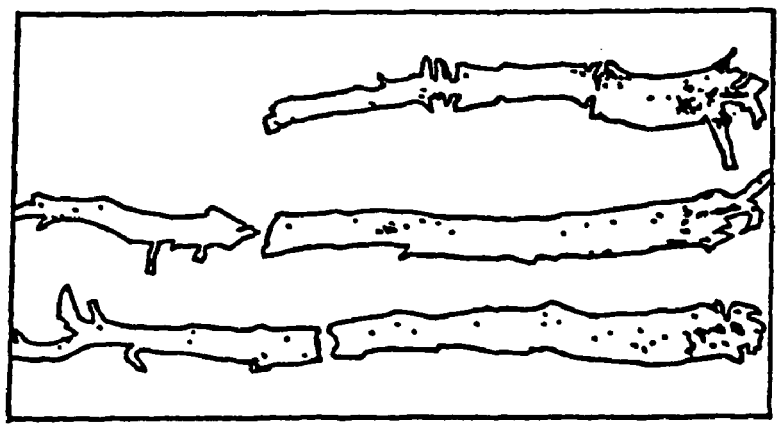

The 9-week-old male apoE knockout mice (apoE(−/−); purchased from The Jackson Laboratory) were divided into three groups of control/rapeseed (rapeseed meal extract administration group)/safflower (safflower meal extract administration group) with 9 mice per group, and each group was allowed free intake of a feed having ingredients shown in Table 5 for 5 weeks. The mice were sacrificed at week 2 (n=6) and week 5 (n=3), a part of the aorta from the aortic root to the femoral artery bifurcation was removed, and the area of atheromatous plaque (plaque) formed on the vascular inner wall stained with Sudan IV was compared with that of the control group. By 2 weeks' administration, plaque formation was tended to be suppressed in the rapeseed group and safflower group as compared to the control group. By comparison of groups after extended administration for 3 weeks thereafter, the above-mentioned tendency became stronger (plaque area: safflower<rapeseed<control), and an effect of suppressing formation of initial lesion of atherosclerosis was exhibited by these oil plant meal extracts (see, FIG. 2).

TABLE 5

| Group | Ingredients of feed |
|---|---|
| control | Normal diet (20% (w/w) vitamin-free casein, 66.3% starch, 5% corn oil, 3.5% AIN-93-mineral mixture, 1% AIN-93-vitamin mixture, 0.2% choline chloride, 4% cellulose powder) |
| rapeseed | Normal diet + 1.3% (w/w) rapeseed meal extract* *balanced with starch |
| safflower | Normal diet + 1.0% (w/w) safflower meal extract* *balanced with starch |

Reference Example 3

Figure 3:
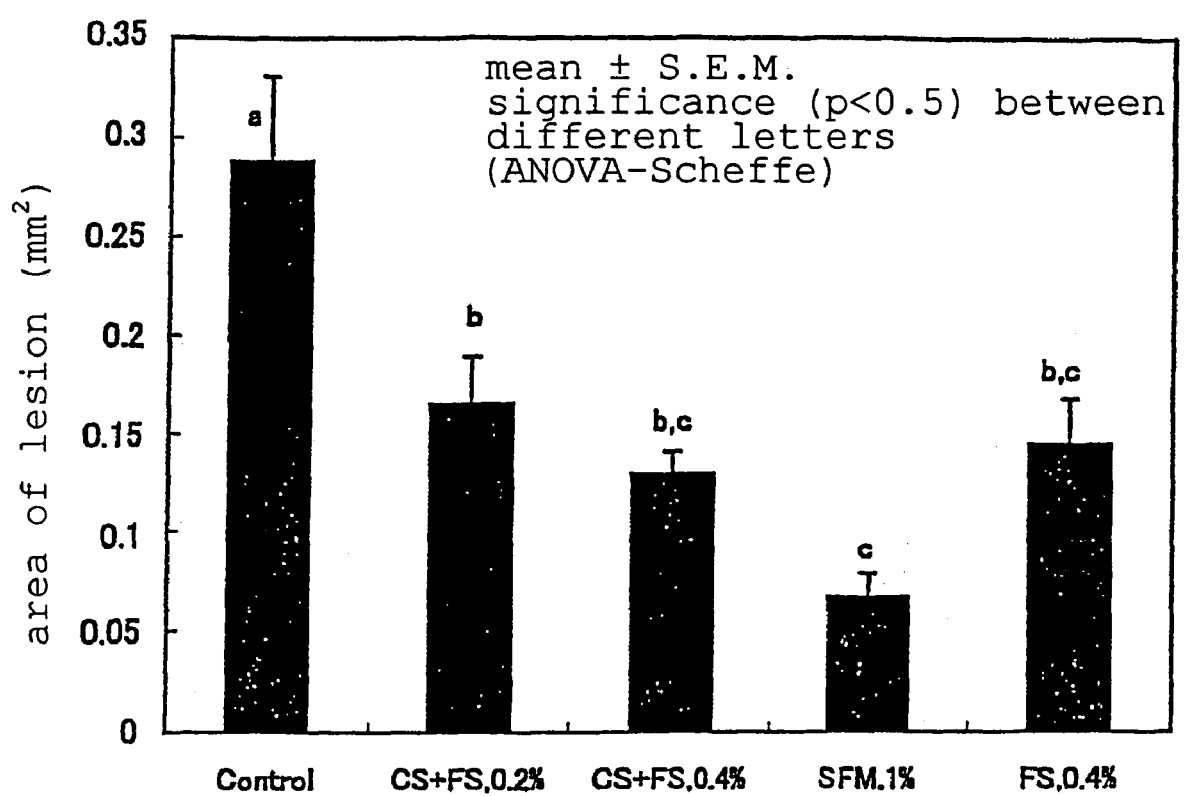
FIG. 3 is a graph showing an aortic root lesion area in apoE knockout mice (21-week-old, male, week 15 of administration of each sample) in Reference Example 3, wherein SFM is a safflower meal extract composition, CS is p-coumaroylserotonin, and FS is feruloylserotonin.

The 6-7-week-old male apoE knockout mice (purchased from The Jackson Laboratory) were divided into five groups of:

(1) control (Control);

(2) serotonin derivative 0.2 wt % administration (p-coumaroylserotonin (CS), feruloylserotonin (FS), 0.1% each) (CS+FS, 0.2%);

(3) serotonin derivative 0.4 wt % administration (p-coumaroylserotonin (CS), feruloylserotonin (FS), 0.2% each) (CS+FS, 0.4%);

(4) feruloylserotonin (FS) 0.4 wt % administration (FS, 0.4%); and (5) safflower meal extract (SFM) 1 wt % administration (SFM, 1%), with 7 to 10 mice per group, and each group was allowed free intake of the feed having ingredients shown in Table 6 for 15 weeks. The safflower meal extract (SFM) used in this Reference Example was prepared according to the method shown in Reference Example 2. After the completion of the administration period, the mice were sacrificed, the aortic root was sliced, and the lipid deposition part (atherosclerosis lesion) was stained with Oil Red O. Three slices were prepared for one individual and the samples most clearly showing the aortic valve were subjected to image analysis (using WinROOF (MITANI CORPORATION)) and the area of the lesion was measured based on the method of Rajendra et al (*J. Lipid Res.*, vol. 36, pp. 2320-2328 (1995)). The obtained area of the lesion was subjected to an analysis of variance between respective groups, and when a significant difference was observed, the average values were compared between groups by the Scheffe test. While the serotonin derivatives (Zhang et al, *Chem. Pharm. Bull.* vol. 44, pp. 874-876 (1996) and Kawashima et al, *J. Interferon Cytokine Res.*, vol. 18, pp. 423-428 (1998)), main phenolic substances in safflower meal known to have antioxidant activity and anti-inflammatory activity in vitro, partially suppressed lesion formation in apoE knockout mice, a safflower meal extract (SFM, containing 10 to 30 wt % of serotonin derivatives) was found to provide even stronger suppression than the serotonin derivatives (see, FIG. 3).

TABLE 6

| Composition | g (in 1 kg of feed) | | | | |
|---|---|---|---|---|---|
| | Control | CS + FS, 0.2% | CS + FS, 0.4% | SFM, 1% | FS, 0.4% |
| vitamin-free casein | 200.0 | 200.0 | 200.0 | 200.0 | 200.0 |
| corn starch | 632.5 | 630.5 | 628.5 | 622.5 | 628.5 |
| corn oil | 70.0 | 70.0 | 70.0 | 70.0 | 70.0 |
| mineral mixture (AIN-93G) | 35.0 | 35.0 | 35.0 | 35.0 | 35.0 |
| vitamin mixture (AIN-93G) | 10.0 | 10.0 | 10.0 | 10.0 | 10.0 |
| choline bitartrate | 2.5 | 2.5 | 2.5 | 2.5 | 2.5 |
| cellulose powder | 50.0 | 50.0 | 50.0 | 50.0 | 50.0 |
| p-coumaroyl-serotonin | 0.0 | 1.0 | 2.0 | 0.0 | 0.0 |
| feruloyl-serotonin | 0.0 | 1.0 | 2.0 | 0.0 | 4.0 |
| safflower meal extract | 0.0 | 0.0 | 0.0 | 10.0 | 0.0 |
| total | 1000.0 | 1000.0 | 1000.0 | 1000.0 | 1000.0 |

INDUSTRIAL APPLICABILITY

From what has been described in the foregoing, it is clear that the plant seed extract compositions of the present invention are remarkably effective for the prophylaxis of atherosclerosis. Moreover, since the plant seed extract compositions of the present invention contain materials derived from natural sources, they are highly safe and are almost free of side effects. Therefore, the foods, feeds, and pharmaceutical compositions of the present invention are free of practical problems and are advantageous. Furthermore, the method of the present invention is effective for obtaining the plant seed extract composition of the present invention having a high content of the active ingredient and a low content of diarrhea-inducing substances.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A safflower seed extract composition, which is prepared by a process comprising:
   (i) washing a defatted safflower seed with water, to obtain a washed product;
   (ii) separating the washed product from a resulting washing liquid; and
   (iii) extracting the washed product with an organic solvent;
   wherein:
   washing is carried out using water having a temperature of 5 to 45° C.; and
   the organic solvent comprises at least one member selected from the group consisting of alcohols having 1 to 4 carbon atoms.

2. The composition of claim 1, wherein the organic solvent comprises ethanol.

3. A safflower seed extract composition, which is prepared by a process comprising:
   (i) washing a defatted safflower seed with water, to obtain a washed product;
   (ii) separating the washed product from a resulting washing liquid;
   (iii) extracting the washed product with an organic solvent, to obtain an extract; and
   (iv) concentrating and drying the extract;
   wherein:
   washing is carried out using water having a temperature of 5 to 45° C.; and
   the organic solvent comprises at least one member selected from the group consisting of alcohols having 1 to 4 carbon atoms.

4. The composition of claim 3, wherein the organic solvent comprises ethanol.

5. A safflower seed extract composition, wherein the weight ratio of (a) the total content of p-coumaroylserotonin, feruloylserotonin, p-coumaroylserotonin glycoside, and feruloylserotonin glycoside to (b) 2-hydroxyarctiin is 1:0.01 to 0.2.

6. The composition of claim 5, which is prepared by a process comprising:
   (i) washing a defatted safflower seed with water, to obtain a washed product;
   (ii) separating the washed product from a resulting washing liquid; and
   (iii) extracting said washed product with an organic solvent;
   wherein:
   washing is carried out using water having a temperature of 5 to 45° C.; and
   the organic solvent comprises at least one member selected from the group consisting of alcohols having 1 to 4 carbon atoms.

7. The composition of claim 6, wherein the organic solvent comprises ethanol.

8. The composition of claim 5, which is prepared by a process comprising:
   (i) washing a defatted safflower seed with water, to obtain a washed product;
   (ii) separating the washed product from a resulting washing liquid;
   (iii) extracting said washed product with an organic solvent, to obtain an extract; and
   (iv) concentrating and drying said extract;
   wherein:
   washing is carried out using water having a temperature of 5 to 45° C.; and
   the organic solvent comprises at least one member selected from the group consisting of alcohols having 1 to 4 carbon atoms.

9. The composition of claim 8, wherein the organic solvent comprises ethanol.

10. A food, comprising the composition of claim 1.

11. A food, comprising the composition of claim 3.

12. A food, comprising the composition of claim 5.

13. A feed, comprising the composition of claim 1.

14. A feed, comprising the composition of claim 3.

15. A feed, comprising the composition of claim 5.

16. A pharmaceutical composition, comprising the composition of claim 1 and a pharmaceutically acceptable carrier.

17. A pharmaceutical composition, comprising the composition of claim 3 and a pharmaceutically acceptable carrier.

18. A pharmaceutical composition, comprising the composition of claim 5 and a pharmaceutically acceptable carrier.

19. A method of producing a safflower seed extract composition, which comprises:
(i) washing a defatted safflower seed with water, to obtain a washed product;
(ii) separating the washed product from a resulting washing liquid; and
(iii) extracting said washed product with an organic solvent;

wherein:
washing is carried out using water having a temperature of 5 to 45° C.; and
the organic solvent comprises at least one member selected from the group consisting of alcohols having 1 to 4 carbon atoms.

20. The method of claim 19, wherein the organic solvent comprises ethanol.

21. A method of producing a safflower seed extract composition, which comprises:
(i) washing a defatted safflower seed with water, to obtain a washed product;
(ii) separating the washed product from a resulting washing liquid;
(iii) extracting the washed product with an organic solvent, to obtain an extract; and
(iv) concentrating and drying the extract;

wherein:
washing is carried out using water having a temperature of 5 to 45° C.; and
the organic solvent comprises at least one member selected from the group consisting of alcohols having 1 to 4 carbon atoms.

22. The method of claim 21, wherein the organic solvent comprises ethanol.

23. A method for reducing the risk of developing atherosclerosis or a disease caused by atherosclerosis in a subject, comprising administering an effective amount of a composition according to claim 1 to said subject.

24. A method for reducing the risk of developing atherosclerosis or a disease caused by atherosclerosis in a subject, comprising administering an effective amount of a composition according to claim 3 to said subject.

25. A method for reducing the risk of developing atherosclerosis or a disease caused by atherosclerosis in a subject, comprising administering an effective amount of a composition according to claim 5 to said subject.

* * * * *